(12) United States Patent
Qiu et al.

(10) Patent No.: US 8,852,755 B2
(45) Date of Patent: Oct. 7, 2014

(54) OXADIAZOLE METALLIC COMPLEXES AND THEIR ELECTRONIC AND OPTO-ELECTRONIC APPLICATIONS

(75) Inventors: Chunong Qiu, Brossard (CA); Steven Xiao, Laval (CA); Cindy Xing Qiu, Brossard (CA)

(73) Assignee: Merck Patent GmbH (DE)

( * ) Notice: Subject to any disclaimer, the term of this patent is extended or adjusted under 35 U.S.C. 154(b) by 295 days.

(21) Appl. No.: 10/917,474

(22) Filed: Aug. 13, 2004

(65) Prior Publication Data
US 2006/0036097 A1 Feb. 16, 2006

(51) Int. Cl.
| | |
|---|---|
| C09K 11/06 | (2006.01) |
| H01L 51/54 | (2006.01) |
| H01L 51/46 | (2006.01) |
| C07D 271/10 | (2006.01) |
| C07F 15/00 | (2006.01) |
| H01L 51/00 | (2006.01) |
| H05B 33/14 | (2006.01) |
| H01L 51/50 | (2006.01) |

(52) U.S. Cl.
CPC .......... C09K 11/06 (2013.01); *C09K 2211/1048* (2013.01); C07D 271/10 (2013.01); C07F 15/0033 (2013.01); H01L 51/0085 (2013.01); *C09K 2211/185* (2013.01); *Y02E 10/549* (2013.01); H05B 33/14 (2013.01); *H01L 51/5016* (2013.01); *C09K 2211/1029* (2013.01); *Y10S 428/917* (2013.01)
USPC ........... 428/690; 428/917; 313/504; 135/263; 257/E51.044; 548/103; 544/225; 546/4; 546/5; 546/10

(58) Field of Classification Search
USPC ......................................................... 548/103
See application file for complete search history.

(56) References Cited

U.S. PATENT DOCUMENTS

| | | | |
|---|---|---|---|
| 5,844,363 | A | 12/1998 | Gu et al. |
| 6,303,238 | B1 | 10/2001 | Thompson et al. |
| 6,660,410 | B2 | 12/2003 | Hosokawa |
| 2001/0019782 | A1* | 9/2001 | Igarashi et al. ............... 428/690 |
| 2002/0064681 | A1 | 5/2002 | Takiguchi et al. |
| 2002/0119294 | A1 | 8/2002 | Monkarsh et al. |
| 2002/0139279 | A1 | 10/2002 | Emanuel |
| 2002/0182441 | A1 | 12/2002 | Lamansky et al. |

FOREIGN PATENT DOCUMENTS

JP      04363894      12/1992

OTHER PUBLICATIONS

Holger Spanggaard and Frederik Krebs, Solar Energy Materials and Solar Cells, 204, 125-146.
M.A. Baldo, S. Lamansky, P.E. Burrows, M.E. Thompson and S.R. Forrest, Applied Physics Letter, 1999, 75, 4-6.

* cited by examiner

*Primary Examiner* — Marie R. Yamnitzky
(74) *Attorney, Agent, or Firm* — Drinker Biddle & Reath LLP

(57) ABSTRACT

The present invention relates to oxadiazole metallic complexes. More specifically it relates to the synthesis and electronic and opto-electronic applications of oxadiazole metallic complexes having a general Formula I, wherein each of variables is defined herein.

21 Claims, 6 Drawing Sheets

(a)

(b)

(a)

(b)

(a)

(b)

(a)

(b)

(a)

(b)

OXADIAZOLE METALLIC COMPLEXES AND THEIR ELECTRONIC AND OPTO-ELECTRONIC APPLICATIONS

FIELD OF THE INVENTION

The present invention relates to oxadiazole metallic complexes. More specifically it relates to the synthesis oxadiazole metallic complexes and the applications of oxadiazole metallic complexes.

BACKGROUND OF THE INVENTION

Phosphorescent materials having light emitting and charge transport properties are increasingly desirable for organic electronic and opto-electronic devices include organic light emitting devices (OLEDs), organic phototransistors, organic thin film transistors (OTFT), organic chemical sensors, organic photovoltaic cells (solar cells), and organic photo detectors.

Of the variety of electronic and opto-electronic applications of phosphorescent materials, organic light emitting diodes (OLED) are the most attractive for flat display and general lighting industry. OLEDs make use of thin organic films that emit light when voltage is applied across the device. For OLED applications, phosphorescent materials are potentially more attractive over fluorescent materials as the former may make use of triplet emission and yield nearly 100% internal quantum efficiency [M. A. Baldo, S. Lamansky, P. E. Burrows, M. E. Thompson and S. F. Forrest, Applied Physics Letter., 1999, 75, 4]. Most of phosphorescent materials investigated for OLED devices are based on phenyl-pyridine ligand [Takao Takiguchi, et al., US2002064681]. The most popular one is tris(2-phenylpyridine)iridium (Irppy), which has been successfully employed in fabrication of green OLED devices. However, this is not the case for other colors from phosphorescent materials based on phenylpyridine ligand. The well-known blue phosphorescent material based on phenylpyridine ligand is iridium(III)bis(2-(4,6-difluorophenyl)pyridinato)picolinate (Firpic) [S. Lamanski, et al, US2002182441], which suffers from a short life-span and low efficiencies.

Therefore, the need for new phosphorescent materials are highly desirable for the commercialization of the organic electronics, OLED in particularly. In search for high performance phosphorescent materials, researchers around the world have explored variety of iridium complexes based on ligands such as benzoquinoline (bzq), phenylbenzothiazole (bt), naphthylbenzothiazole (bsn), phenylquinoline (pq), thienylpyridine (thp), benzothienylpyridine (btp), phenyloxazole (op), diphenyloxazole (dpo), phenyl-isoquinoline (piq) and many others. Although significant progresses have being made though various structure modifications, there is still a need for better materials with novel structures.

It is well know that oxadiazole derivatives have appreciable electron transport properties, and they have been successfully employed in many OLED device configurations [Saito Shogo, et al., JP04363894]. Using oxadiazole derivatives to make metal complexes is expected to improve charge transfer between ligand and metal, ultimately enhance the performance of the opto-electronic devices. However, oxadiazole based compounds have not been employed to make metal complexes for phosphorescent materials.

SUMMARY OF THE INVENTION

One objective of this invention is to provide a new class of phosphorescent materials for electronic and opto-electronic devices, based on oxadiazole ligand. The invented metallic complexes have a general Formula I:

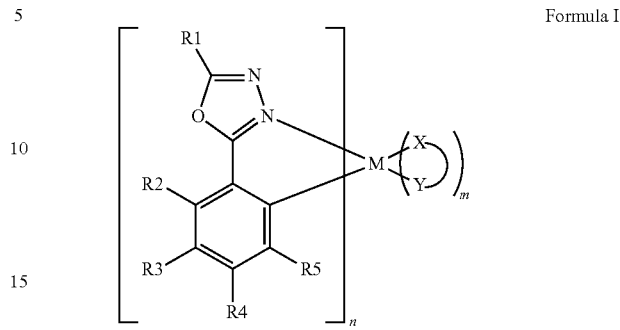

The present invention also teaches a general method for preparation of metal complexes of Formula I.

The present invention further discloses the applications of metal complexes of Formula I and the fabrication of electronic and opto-electronic devices, including light emitting devices, solar cells and phosphorescence devices.

DETAILED DESCRIPTION OF THE PREFERRED EMBODIMENTS

Figure 1:
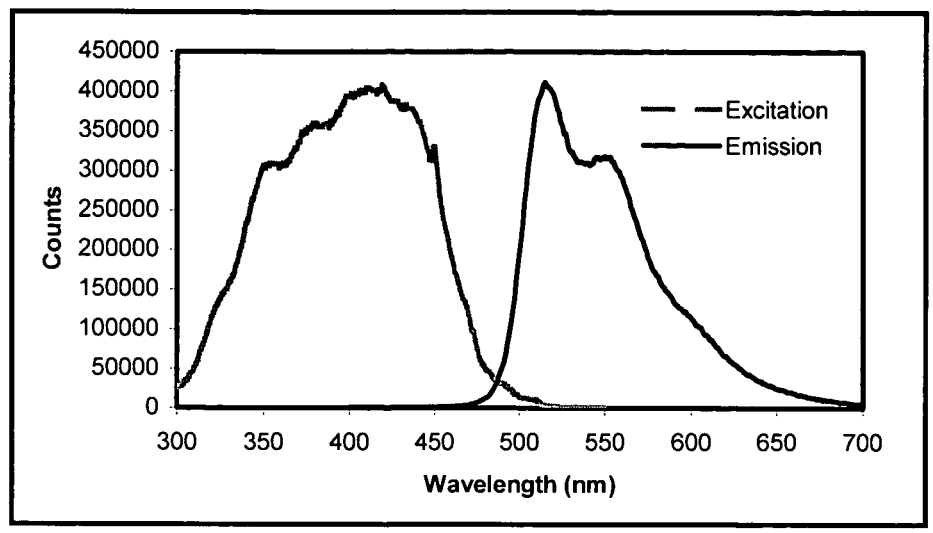
FIG. 1 shows photoluminescence spectra of compound I $(odz)_2Ir(acac)$ (a) in DCM and (b) in THF.
Figure 1:
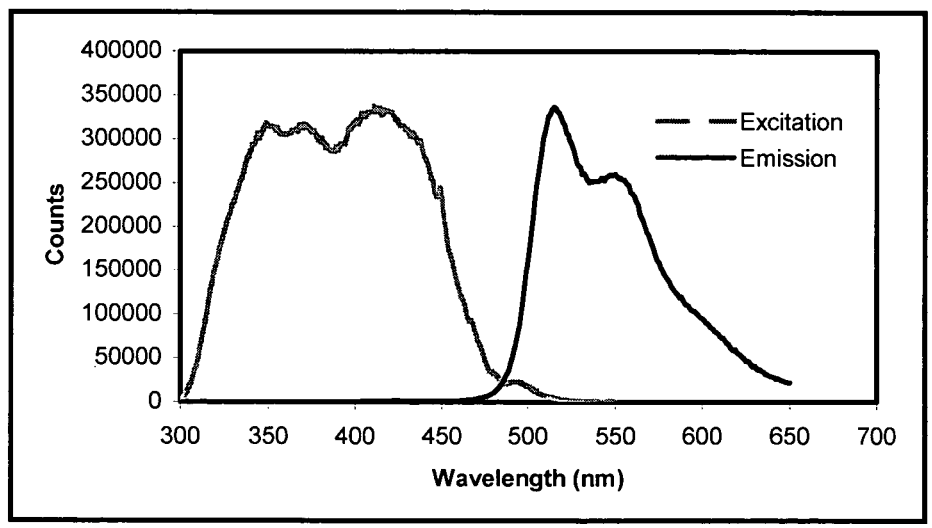

Generally, a phosphorescent transition may be observed from an excited metal-to-ligand charge transfer (MLCT) state of an organometallic molecule such as tris(2-phenylpyridine)iridium(III). In order to facilitate the metal-to-ligand charge transfer (MLCT), an energy match between metal atom in the center and HOMO-LUMO level of ligand is required. For this reason, we have invented a class of metal complexes with a general Formula I:

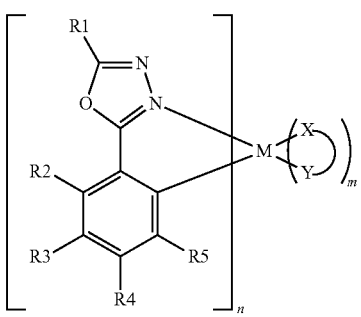

Formula I

In this formula, M is a metal with an atomic weight of greater than 40, n is 1, 2, or 3, and m is 0, 1, or 2, and m+n is equal or greater than 3. Each of R1, R2, R3, R4, and R5 is, independently, H, alkyl, alkenyl, alkynyl, aryl, alkylaryl, CN, perfluoroalkyl, trifluorovinyl, $CO_2R$, $C(O)R$, $NR_2$, $NO_2$, OR, halo, heteroaryl, substituted aryl, substituted heteroaryl or a heterocyclic group; And additionally or alternatively, any one or more of R2 and R3 or R3 and R4, or R4 and R5 together form, independently, a fused 5- to 6-member cyclic group, where the cyclic group is cycloalkyl, cycloheteroalkyl, aryl, or heteroaryl, and where the fused 5- to 6-member cyclic group may be optionally substituted with one or more of alkyl, alkenyl, alkynyl, alkylaryl, CN, perfluoroalkyl, trifluorovinyl, $CO_2R$, $C(O)R$, $NR_2$, $NO_2$, OR, halo; each R is independently H, alkyl, alkenyl, alkynyl, alkylaryl, and aryl; X and Y together, X^Y, represents a ligand which can form chemical and/or co-ordination bonds with the metal atom, M.

In one embodiment of the present invention, X^Y is a bidentate ligand, which contains at least one oxygen atom that can form chemical bond with the metal atom, M. Such bidentate ligands are known to those skilled in the art. In some embodiments, bidentate ligands are monoanionic. Suitable bidentate ligands include acetylacetonate (acac), picolinate (pic), salicylidene, amino acids, salicylaldehydes, and iminoacetonates, and derivatives thereof. Of these, more preferred bidentate ligands include acetylacetonate (acac) and picolinate (pic), and derivatives thereof. For example only, a few typical core structures of these preferable ligands are listed in Table-1 below.

TABLE 1

Core structure of ligand having oxygen atom that can bond the metal atom, M

| | |
|---|---|
| acac | 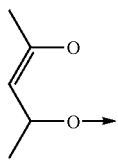 |
| pic | 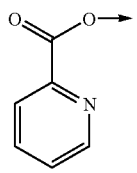 |

In another embodiment of the invention, X^Y is a bidentate ligand which contains at least one carbon atom that can form chemical bond with the metal atom, M. Such bidentate ligands are also known to those skilled in the art. These suitable bidentate ligands include phenylpyridine (ppy), benzoquinoline (bzq), phenylbenzothiazole (bt), naphthylbenzothiazole (bsn), phenylquinoline (pq), thienylpyridine (thp), benzothienylpyridine (btp), phenyloxazole(op), diphenyloxazole (dpo), phenyl-isoquinoline (piq), dibenzoquinoxaline (dbq), phenylpyrazole (ppz), phenyloxazole (poz), phenyltriazole (ptz), and derivatives thereof. Of these, more preferred bidentate ligands include phenylpyridine (ppy), dibenzoquinoxaline (dbq), benzoquinoline (bzq), phenylbenzothiazole (bt), phenylquinoline (pq), benzothienylpyridine (btq), phenylpyrazole (ppz) and phenyl-isoquinoline (piq), phenyloxazole (poz), phenyltriazole (ptz) and derivatives thereof. For example only, a few typical core structures of these preferable ligands are listed in Table-2 below.

TABLE 2

Core structure of ligand having carbon atom that can bond the metal atom, M

| | |
|---|---|
| ppy | 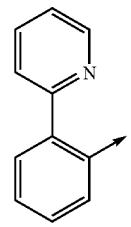 |
| bzq | 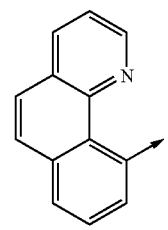 |
| bt | 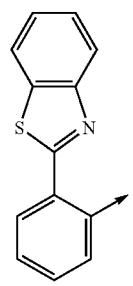 |
| pq | 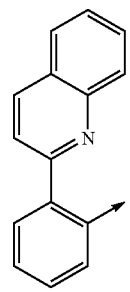 |

TABLE 2-continued

Core structure of ligand having carbon atom that can bond the metal atom, M piq
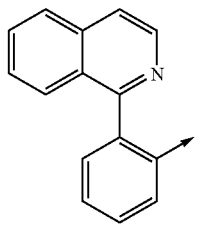

dbq
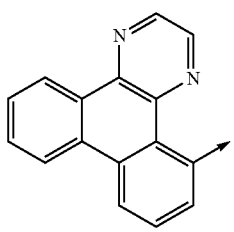

ppz
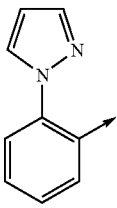

poz
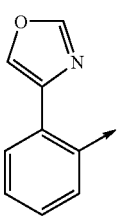

ptz
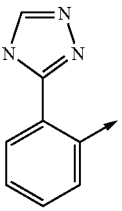

In still another embodiment of the invention, X^Y is a bidentate ligand that contains at least one nitrogen atom that can form coordination bond with the metal atom, M. Such bidentate ligands are also known to those skilled in the art. The preferred ligands of this class include 2,2'-bipyridine (bpy), 1,10-phenanthroline (pat), and derivatives thereof.

According to compounds of the present invention, M can be of any metal atoms, including transition metals, lanthanides, actinides, main group metals, alkali metals and alkaline earth metals. In one preferred embodiment, M is a transition metal and in a more preferred embodiment, M is a second or third row transition metal. In some embodiments, M is Ir, Os, Pt, Pb, Re, or Ru and in a particularly preferred embodiment, M is Ir.

In a further preferred embodiment, this invention comprises the compound of the Formula I in which m is 1 and n is 2, to give a compound of the Formula II Formula II
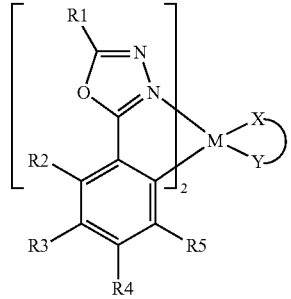

Wherein M, R1, R2, R3, R4 and R5, X and Y are as described for the compound of the Formula I.

Another embodiment of the invention comprises the compound of the Formula I in which m is 0 and n is 3, resulting in a compound of the Formula III Formula III
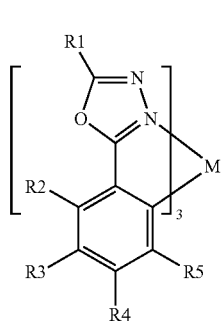

Wherein M, R1, R2, R3, R4 and R5 are as described for the compound of the Formula I.

The names or terms of chemical groups as used, herein are of common concepts to chemists. For examples, the term "halo" or "halogen" includes fluorine, chlorine, bromine and iodine.

The term "alkyl" as used herein contemplates both straight and branched chain alkyl radicals. Preferred alkyl groups are those containing from one to fifteen carbon atoms and includes methyl, ethyl, propyl, isopropyl, butyl, isobutyl, tert-butyl, and the like. Additionally, the alkyl group may be optionally substituted with one or more substituents selected from halo, CN, $CO_2R$, C(O)R, $NR_2$, cyclic-amino, $NO_2$, and OR.

The term "cycloalkyl" as used herein contemplates cyclic alkyl groups. Preferred cycloalkyl groups are those containing 3 to 7 carbon atoms and include cyclopropyl, cyclopentyl, cyclohexyl, and the like. Additionally, the cycloalkyl group may be optionally substituted with one or more substituents selected from halo, CN, $CO_2R$, $C(O)R$, $NR_2$, cyclic-amino, $NO_2$, and OR.

The term "alkenyl" as used herein contemplates both straight and branched chain alkene radicals. Preferred alkenyl groups are those containing two to fifteen carbon atoms. Additionally, the alkenyl group may be optionally substituted with one or more substituents selected from halo, CN, $CO_2R$, $C(O)R$, $NR_2$, cyclic-amino, $NO_2$, and OR.

The term "alkynyl" as used herein contemplates both straight and branched chain alkyne radicals. Preferred alkyl groups are those containing two to fifteen carbon atoms. Additionally, the alkynyl group may be optionally substituted with one or more substituents selected from halo, CN, $CO_2R$, $C(O)R$, $NR_2$, cyclic-amino, $NO_2$, and OR.

The term "alkylaryl" as used herein contemplates an alkyl group which has as a substituent an aromatic group. Additionally, the alkylaryl group may be optionally substituted on the aryl with one or more substituents selected from halo, CN, $CO_2R$, $C(O)R$, $NR_2$, cyclic-amino, $NO_2$, and OR.

The term "heterocyclic group" as used herein contemplates non-aromatic cyclic radicals. Preferred heterocyclic groups are those containing 3 or 7 ring atoms which includes at least one hetero atom, and includes cyclic amines such as morpholino, piperdino, pyrrolidino, and the like, and cyclic ethers, such as tetrahydrofuran, tetrahydropyran, and the like.

The term "aryl" or "aromatic group" as used herein contemplates single-ring aromatic groups and polycyclic ring systems. The polycyclic rings may have two or more rings in which two carbons are common by two adjoining rings (the rings are "fused") wherein at least one of the rings is aromatic, e.g., the other rings can be cycloalkyls, cycloalkenyls, aryl, heterocycles and/or heteroaryls.

The term "heteroaryl" as used herein contemplates single-ring hetero-aromatic groups that may include from one to three heteroatoms, for example, pyrrole, furan, thiophene, imidazole, oxazole, thiazole, triazole, pyrazole, pyridine, pyrazine and pyrimidine, and the like. The term heteroaryl also includes polycyclic hetero-aromatic systems having two or more rings in which two atoms are common to two adjoining rings (the rings are "fused") wherein at least one of the rings is a heteroaryl, e.g., the other rings can be cycloalkyls, cycloalkenyls, aryl, heterocycles and/or heteroaryls.

Metal complexes containing heavy atoms, iridium in particularly, often exhibit strong triplet emission (phosphorescence) created by spin-orbit coupling. The fabrication of opto-electronic devices, organic light emitting diodes (OLEDs) in particularly, by making use of these phosphorescent metal complexes is well known to those skilled in the art. A simple device may be fabricated by sandwiching these metal complexes between two electrodes (the anode and the cathode), forming a single layer organic light emitting diode. For high efficiency devices, other layers including hole transport layer, electron transporting layer, electron injection layer, etc, are often required. The material selection and functionality of the selected materials for each layer have been extensively studied. Several examples are described in U.S. Pat. Nos. 5,844,363, 6,303,238, and 6,660,410, which are incorporated herein by reference in their entirety.

Due to possible self-quenching of phosphorescent materials in high concentration or in aggregate form, it is preferred to blend these materials with other materials with high energy gap to form the emission layer. In this case, the high energy gap materials are referred to as hosts and these phosphorescent materials are referred to as dopants. The hosts can be either small molecules or polymers. Suitable small molecular hosts include BCP (2,9-dimethyl-4,7-diphenyl-1,10-phenanthroline), mCP (1,3-N,N-dicarbozolebenzebe), CBP (4,4'-N'N-dicarbazole-biphenyl), and other carbazole compounds. The suitable polymeric hosts include PVK (poly-9-vinylcarbozole), PF (poly(fluorene)), PPP (poly(p-phenylene)), PPV (poly(p-phenylenevinylene)), and others.

It is critical to control the concentration of these phosphorescent materials (or dopants) in any host material. The preferable concentration is 0.5%-25%, more specifically, 2%-10%.

Metal complexes containing heavy atoms, iridium in particularly, are also know to have electron transport properties. By properly using such electron transporting properties, photovoltaic devices or field effect transistors can be configured. For photovoltaic devices, the metal complexes of Formula I according to this invention may function as electron acceptors or light absorbers. A review of the development of solar cell based on organic materials is recently published by Holger Spanggaard and Frederik Krebs in Solar Energy Materials and Solar Cells, 2004, 125, which is incorporated herein by reference in their entirety.

By simply using the photo-luminescent property of the metal complexes of Formula I according to this invention, secure optically readable inks can be formulated for preventing forgery and labeling. As illustrated in the experimental section, different compounds of Formula I has different excitation and emission patterns. These patterns can be used as finger prints for security purposes. The emission colors of these metal complexes are visible and can be detected directly by human eyes. It is also preferable to measure the emission pattern by using a photospectrometer for more precision. The formulations of such inks for different substrates are well known to those skilled in the art. Several examples are described in U.S. patent applications U.S. patents US2002119294 and US2002139279, which are incorporated herein by reference in their entirety.

It is understood that the various embodiments described herein are by way of example only, and are not intended to limit the scope of the invention. For example, many of the materials and structures described herein may be substituted with other materials and structures without deviating from the spirit of the invention.

The synthetic chemistry of oxadiazole is known to those skilled in the art. The present invention will describe a few synthetic procedures in the experimental sections. It is also understood that structures and synthesis methods of these compounds are intended only as illustrative examples and the invention is not to be limited thereto.

EXPERIMENTAL

Specific representative embodiments of the invention will now be described, including how such embodiments may be made. It is understood that the specific methods, materials, conditions, process parameters, apparatus and the like do not necessarily limit the scope of the invention.

Solvents and reagents are purchased from Sigma Aldrich Canada Ltd. The reagents are of the highest purity and are used as received.

Example 1

The Synthesis of Ligand I-(odz)

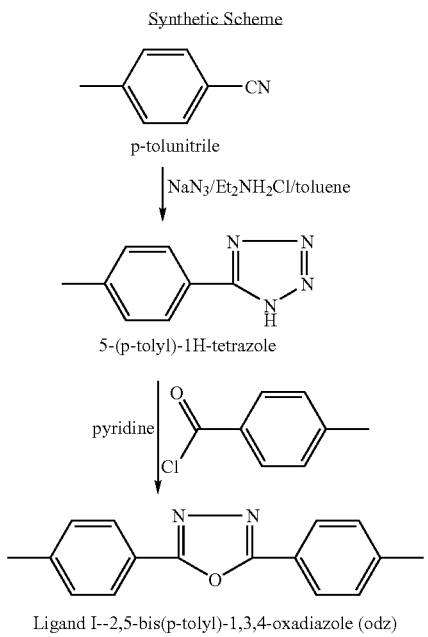

Procedure:

In an environment of nitrogen, a mixture of p-tolunitrile (35.15 g, 300 mmol.), sodium azide (29.25 g, 450 mmol.), diethylamine hydrochloride (49.32 g, 450 mmol), and toluene (500 mL) was refluxed for 12 hours. After it was allowed to cool down, the beige suspension obtained was extracted with water (3×500 mL). Concentrated HCl was then drop-added into the water extracts to reach a pH value of around 3. The resulting white precipitates were filtered and dried in a vacuum oven all night. 5-(p-Tolyl)-1H-tetrazole in a form of white crystals (43.25 g, 90.0%) was obtained and used for the next step without any further purification.

The above-obtained 5-(p-tolyl)-1H-tetrazole (36.84 g, 0.23 mol.), p-toluoyl chloride (42.67 g, 0.276 mol.) and pyridine were mixed together (500 mL) and stirred until the mixture became a homogeneous beige suspension. The suspension was then heated to reflux for more than 12 hours. The resulting brown solution was allowed to cool down to room temperature and was poured into a 1,000 mL of well-stirred icy water. The obtained white precipitate was stirred overnight. The obtained solid was then filtered, washed with water (3×100 mL), dried under suction in the air for overnight and then re-crystallized twice from ethanol/THF. The resulting pale yellow precipitate was allowed to stay in a freezer for overnight and again filtered, washed twice with cool ethanol, and dried under suction and in the air for overnight. Finally, 2,5-bis(p-tolyl)-1,3,4-oxydiazole (Ligand I-odz, 49.50 g, 86.0%) as an off-white crystalline solid was collected.

Example 2

The Synthesis of Dimer I-(odz)$_2$ Ir($\mu$-Cl)$_2$Ir(odz)$_2$

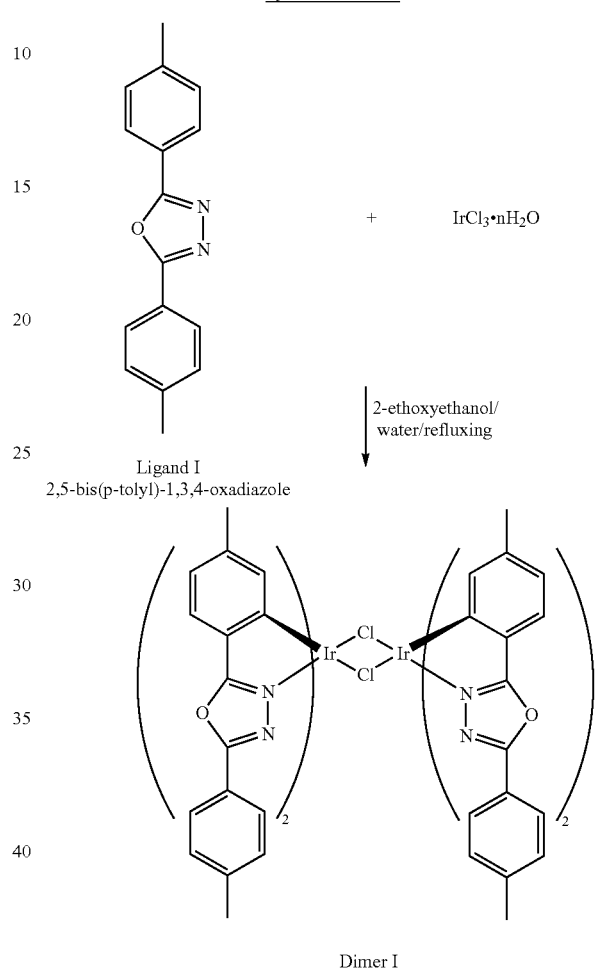

Procedure:

After nitrogen was passed through a 250 mL 3-neck flask for 30 minutes, 115 mL of 2-ethoxyethanol and 35 mL of de-ionized water were poured into the flask and the colorless mixture of solvents was degassed with nitrogen bubbles for 30 minutes. 2,5-bis(p-tolyl)-1,3,4-oxadiazole (Ligand I, 12.52 g, 50 mmol.) and iridium (III) chloride trihydrate (7.05 g, 20 mmol.) were added and the resulting red suspension was heated to reflux for 16 hours.

This suspension was allowed to cool down to room temperature and was stored in a freezer for overnight. The resulting yellow precipitate was filtered, washed with methanol, hexane, and then ether, and dried in the air. Yellow powders (5.40 g, 37.2%) were collected at the end. The NMR results ($^1$HNMR, 400 MHz, CDCl$_3$, $\delta$ ppm) are: 7.82 (d, 8H), 7.39 (d, 4H), 6.96 (d, 8H), 6.66 (d, 4H), 6.31 (s, 4H), 2.33 (s, 12H), 2.04 (s, 12H).

11
Example 3
The Synthesis of Compound I (odz)₂ Ir(acac)

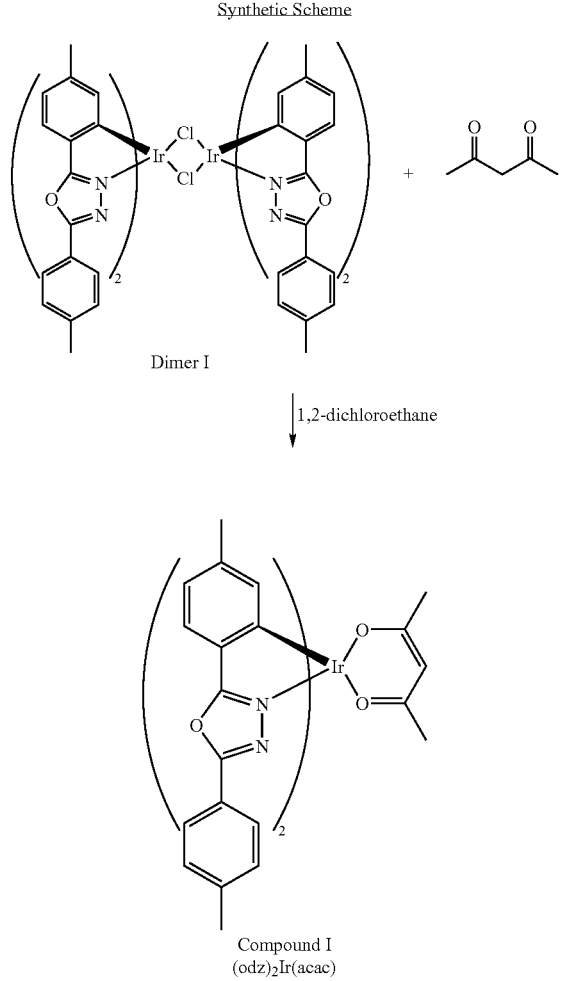

Compound I
(odz)₂Ir(acac)

Procedure:

After nitrogen gas was passed through a 50 mL one-neck flask for 30 minutes, 20 mL of 1,2-dichloroethane, (odz)₂Ir(μ-Cl)₂Ir(odz)₂ (Dimer I, 0.73 g, 0.5 mmol.), 2,4-pentanedione (0.15 g, 1.5 mmol.), and sodium carbonate (0.20 g, 2.0 mmol.) were added into the flask and the resulting yellow mixture was heated to reflux for 24 hours.

The solvent was stripped off by a rotary evaporator, and the yellow solid residue was purified by a silica gel column with dichloromethane as an eluent. A yellow powder was collected (0.44 g, 55.7%). The NMR results (¹HNMR, 400 MHz, CDCl₃, δ ppm) are: 8.12 (d, 4H), 7.48 (d, 2H), 7.37 (d, 4H), 6.72 (d, 2H), 6.52 (s, 2H), 5.23 (s, 1H), 2.45 (s, 6H), 2.17 (s, 6H), 1.90 (s, 6H). FIG. 1 presents photoluminescence spectra of the compound I (odz)₂Ir(acac) (a) in DCM and (b) in THF. It shows a strong emission at 515 nm and 518 nm respectively.

12
Example 4
The Synthesis of Compound II. (oda)₂ Ir(pic)

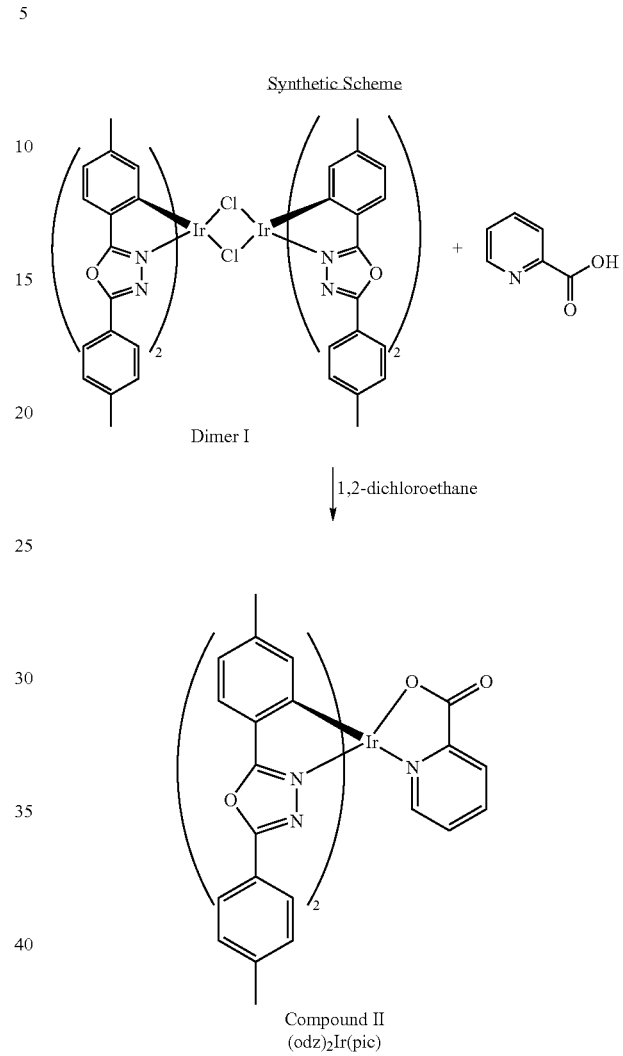

Compound II
(odz)₂Ir(pic)

Procedure:

A 50 mL one-neck flask was fluxed with nitrogen for 30 minutes. 15 mL of 1,2-dichloroethane, (odz)₂Ir(μ-Cl)₂Ir(odz)₂ (Dimer I, 0.29 g, 0.2 mmol.) and picolinic acid (0.05 g, 0.4 mmol.) were added and the resulting yellow mixture was heated to reflux for 24 hours.

Figure 2:
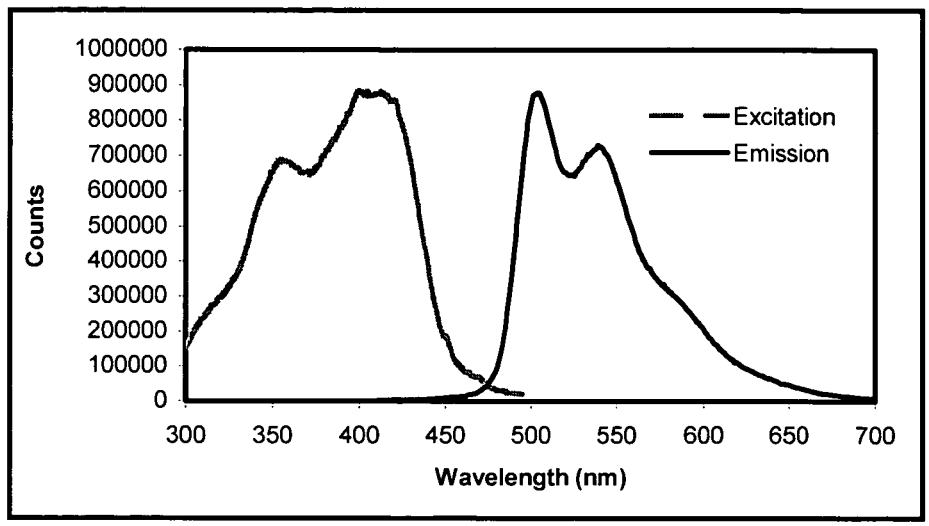
FIG. 2 presents photoluminescence spectra of compound II $(odz)_2Ir(pic)$ (a) in DCM and (b) in THF.
Figure 2:
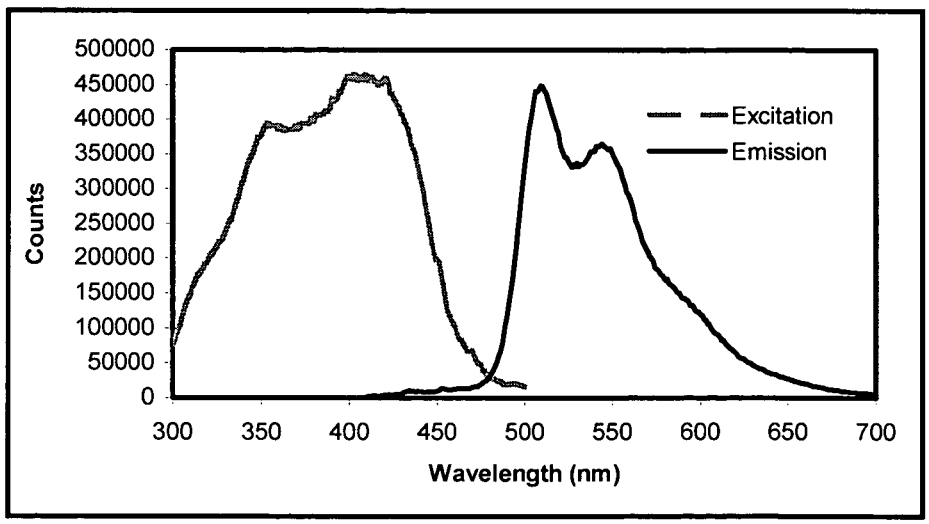

The solvent was stripped off by a rotary evaporator, and the yellow solid residue was purified by a silica gel column with DCM as a first eluent, and methanol as a second eluent to wash the desired product out. A yellow powder was finally collected (0.30 g, 92.3%). The NMR results on the samples (¹HNMR, 400 MHz, CDCl₃, δ ppm) are: 8.28 (m, 1H), 8.07 (d, 2H), 7.87 (m, 4H), 7.53 (dd, 2H), 7.32 (m, 5H), 6.85 (dd, 1H), 6.79 (dd, 1H), 6.66 (s, 1H), 6.53 (s, 1H), 2.45 (s, 6H), 2.18 (s, 6H). FIG. 2 presents photoluminescence spectra of compound II (odz)₂Ir(pic) (a) in DCM and (b) in THF.

Example 5

The Synthesis of Compound III, (odz)₂ Ir(dpm)

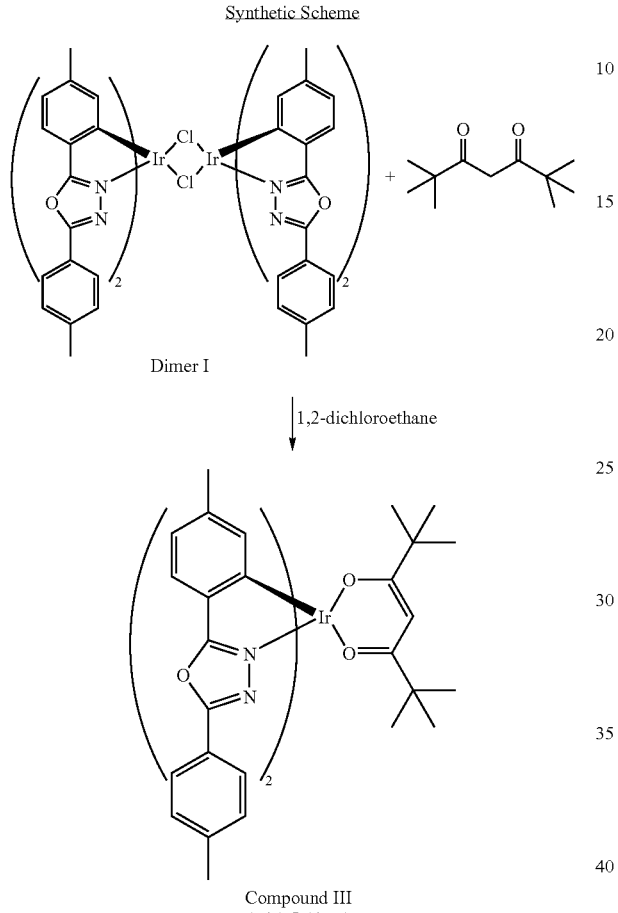

Dimer I

Compound III
(odz)₂Ir(dpm)

Example 6

The Synthesis of Compound IV, Ir(odz)₃

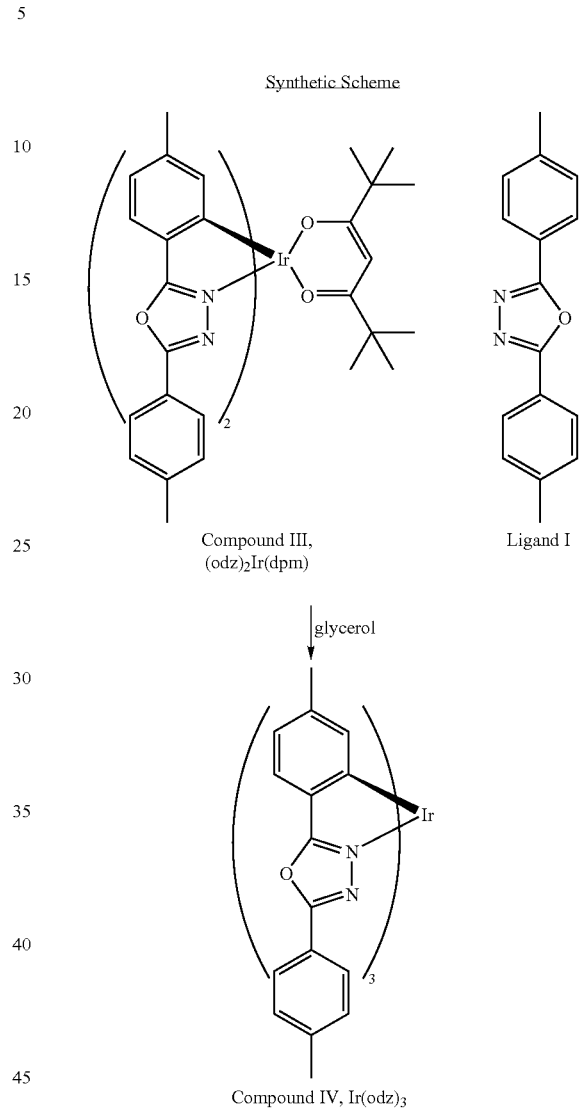

Compound III, (odz)₂Ir(dpm)    Ligand I

Compound IV, Ir(odz)₃

Procedure:

A 100 mL one-neck flask was fluxed with nitrogen for 30 minutes. 40 mL of 1,2-dichloroethane, (odz)₂ Ir(μ-Cl)₂Ir (odz)₂ (dimer I, 3.84 g, 2.64 mmol.), 2,2,6,6-tetramethylheptanedione (1.22 g, 6.6 mmol.), and sodium carbonate (1.40 g, 13.2 mmol.) were added and the resulting deep yellow suspension was heated to reflux for 24 hours.

Figure 3:
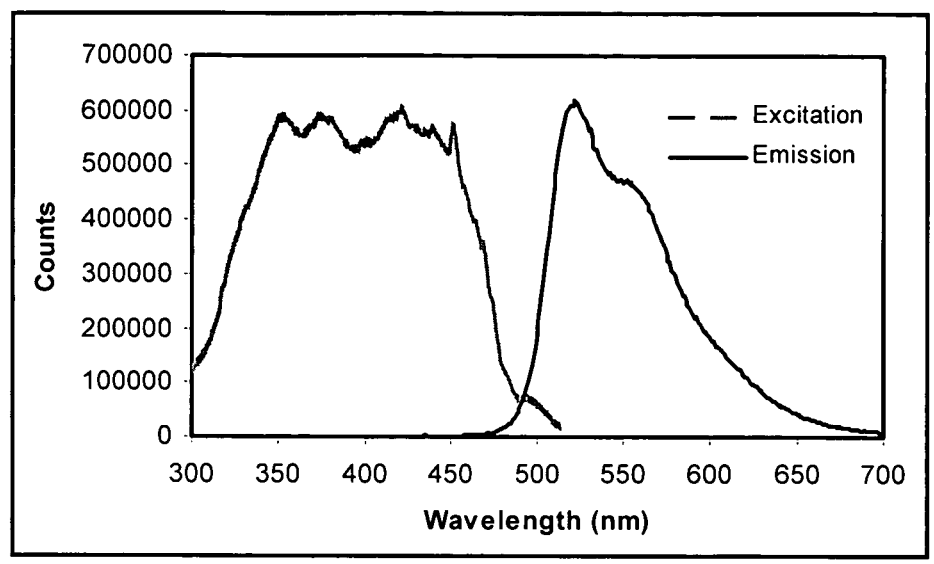
FIG. 3 presents photoluminescence spectra of compound III $(odz)_2Ir(dpm)$ (a) in DCM and (b) in THF.
Figure 3:
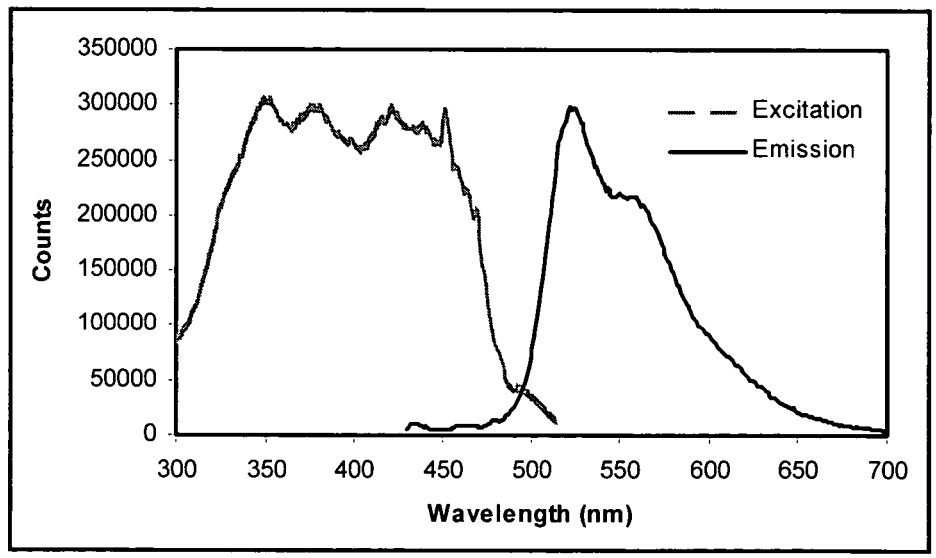

The solvent was stripped off by a rotary evaporator, and the yellow solid residue was purified by a silica gel column with DCM as an eluent. A yellow powder was collected (2.04 g, 44.2%). The NMR results ($^1$HNMR, 400 MHz, CDCl₃, ppm) are: 8.08 (d, 4H), 7.47 (d, 2H), 7.37 (d, 4H), 6.72 (d, 2H), 6.55 (s, 2H), 5.30 (s, 1H), 2.47 (s, 6H), 2.18 (s, 6H), 1.02 (s, 18H). FIG. 3 shows photoluminescence spectra for compound III (odz)₂Ir(dpm) (a) in DCM and (b) in THF. The curves exhibit a shift to a longer wavelength as compared to those for compound II (odz)₂Ir(pic) (FIG. 2) which indicates the tunability of the emission color by varying the ligand.

Procedure:

A 100 mL one-neck flask was fluxed with nitrogen for 30 minutes. 20 mL of glycerol, (odz)₂Ir(dmp) (0.87 g, 1 mmol.), 2,5-bis(p-tolyl)-1,3,4-oxadiazole (Ligand I, 0.50 g, 2 mmol.) were added and the resulting deep yellow solution was heated to reflux for 24 hours.

Figure 4:
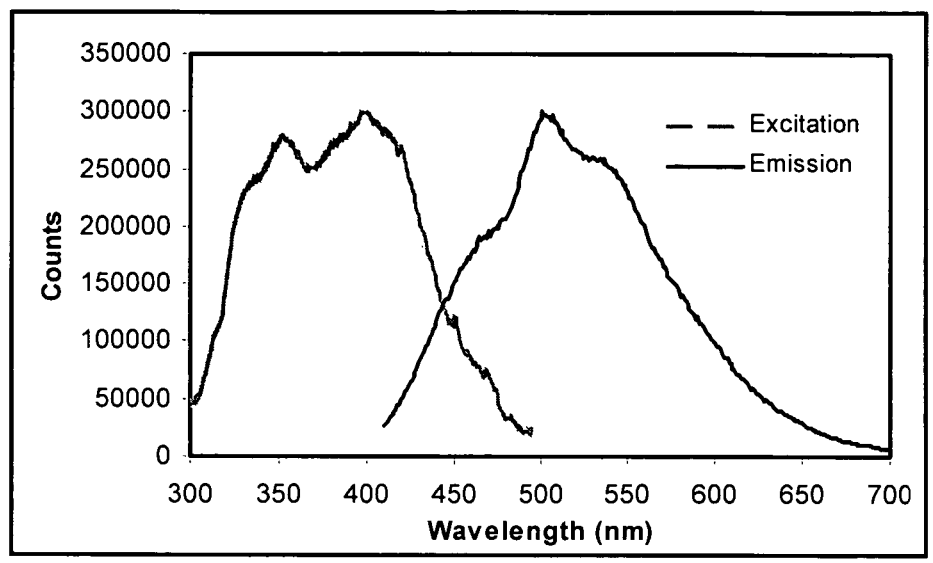
FIG. 4 presents photoluminescence spectra of compound IV $Ir(odz)_3$ (a) in DCM and (b) in THF.
Figure 4:
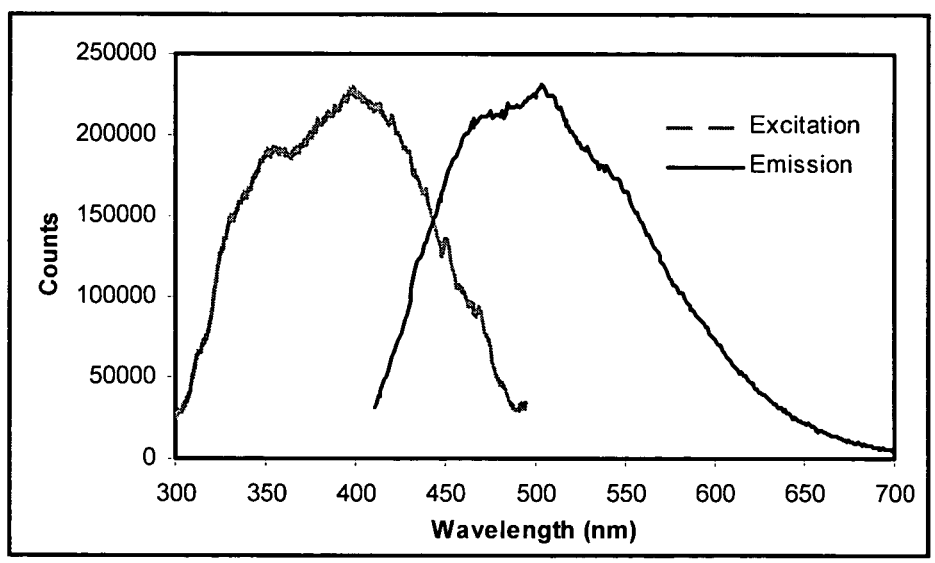

The solvent was then stripped off by a rotary evaporator, and the yellow solid residue was purified by a silica gel column with DCM as an eluent. A yellow powder (0.11 g, 11.7%) was collected at the end. The NMR results ($^1$HNMR, 400 MHz, CDCl₃, δ ppm) are: 7.92 (d, 6H), 7.50 (d, 3H), 6.96 (d, 6H), 6.66 (d, 3H), 6.31 (s, 3H), 2.43 (s, 9H), 2.14 (s, 9H). FIG. 4 illustrates the photoluminescence spectra for compound IV Ir(odz)₃ (a) in DCM and (b) in THF. A strong green emission with a maximum peak located at 499 nm is observed.

Example 7

The Synthesis of Ligand II, (piq)

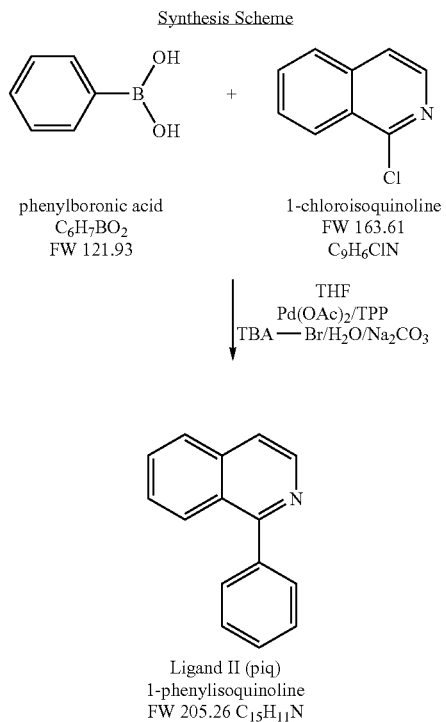

Synthesis Scheme

Ligand II (piq)
1-phenylisoquinoline
FW 205.26 $C_{15}H_{11}N$

Procedure:

A clean 1,000 mL 3-neck flask was fluxed for 30 minutes with nitrogen before 2.26 g of tetrabutylammonium bromide (TBA-Br, 7.0 mmol, 1/20 eq.) was dissolved in a mixture of 120 mL of water and 600 mL of freshly-distilled THF. The resulting colorless mixture was de-aerated with $N_2$ bubbles for 30 minutes. 1.57 g of palladium acetate (7.0 mmol. 1/20 eq.) and 7.34 g of triphenylphosphine (TPP, 28.0 mmmol. 4/20 eq.) were added, and the resulting yellow and clear mixture was stirred to activate the catalysts until it turned into a light yellow suspension (about 30 minutes). Into this suspension, 18.78 g of phenylboronic acid (154.0 mmol, 1.0 eq.), 22.91 g of 1-chloroisoquinoline (140.0 mmol, 1.0 eq.), and 59.35 g of sodium carbonate (0.56 mol, 4.0 eq.) were successively added, and the resulting mixture was re-fluxed (about 24 hours) until TLC monitoring showed 1-chloroisoquinoline was totally consumed (TLC condition, 100% DCM: product Rf=0.37, major by-product Rf=0.95; toluene/hexanes=50/50: product Rf=0.20, major by-product Rf=0.77).

After allowed to cool down, the reaction mixture (light yellow or light red mixture) was totally transferred into a 2,000 mL of separatory funnel. The aqueous layer was separated and extracted with 2×100 mL of THF and 100 mL of ether. The organic layers were combined, washed with 3×50 mL of water, and then stirred with scavenger agent and sodium sulfate overnight. The inorganic salts were removed by filtration, and the yellow filtrate was removed by rotary evaporation. The light yellow solid residue was purified through a chromatography column with toluene/hexanes=50/50 as a first eluent to remove the major by-product, and then 100% DCM to elute the product. 21.61 g of a white crystalline solid was collected (75.2%) after the solvent was evaporated.

The obtained product was characterized by FTIR, NMR, and typical analysis results are:

| | |
|---|---|
| m.p.: | 88-90° C. |
| FTIR (KBr, cm$^{-1}$): | 3433, 3052, 1617, 1581, 1551, 1496, 1439, 1381, 1352, 1318, 1019, 971, 875, 823, 800, 753, 780, 674, 624. |
| $^1$H NMR (CDCl$_3$, δ ppm) | 8.58 (d, 1H), 8.09 (d, 1H), 7.86 (d, 1H), 7.68 (d, 1H), 7.63 (t, 1H), 7.51 (m, 1H). only 6 Hs? |
| $^{13}$C NMR (CDCl$_3$, δ ppm) | 160.4, 142.2, 136.8, 129.9, 129.9, 128.5, 128.3, 127.5, 127.1, 126.9, 126.6, 119.8. only 12 s, should be 13 s. |

Example 8

The Synthesis of Dimer II, -(piq)$_2$ Ir(—Cl)$_2$Ir(piq)$_2$

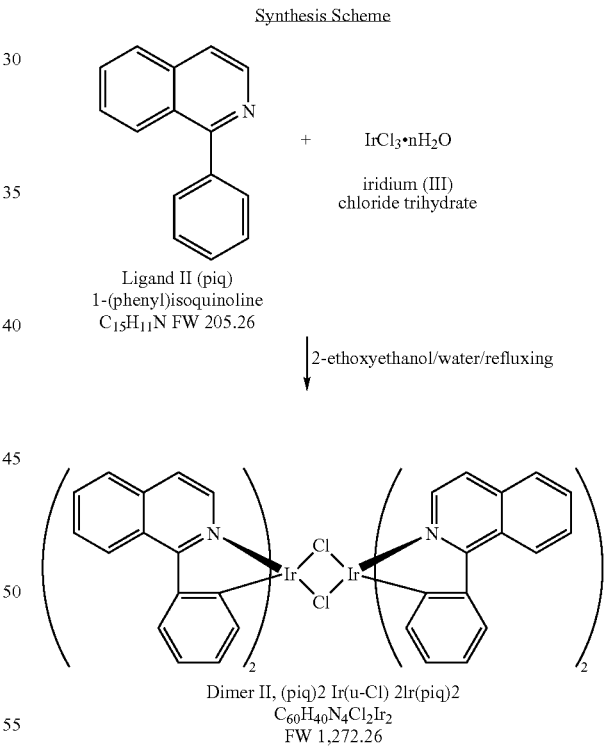

Synthesis Scheme

Ligand II (piq)
1-(phenyl)isoquinoline
$C_{15}H_{11}N$ FW 205.26

Dimer II, (piq)2 Ir(u-Cl) 2Ir(piq)2
$C_{60}H_{40}N_4Cl_2Ir_2$
FW 1,272.26

Procedure:

A 250 mL 3-neck flask was fluxed with nitrogen for 30 minutes. 75 mL of 2-ethoxyethanol and 25 mL of de-ionized water were poured in and the colorless mixture of solvents was de-gassed with nitrogen bubbles for 30 minutes. 7.70 g of 1-phenylisoquinoline (Ligand II (piq), 37.5 mmol, 2.5 eq.) and 5.29 g of iridium (III) chloride trihydrate (15 mmol, 1.0 eq.) were added and the resulting red suspension was heated to reflux for 16 hours.

The suspension was allowed to cool down to room temperature and was stored in a freezer during the night. The resulting red precipitate was filtered, washed twice with methanol, water, hexane, and then ether, and dried in the air for overnight. 8.40 g of red crystalline powder (yield 88.1%) was collected at the end. TLC for the product: 100% DCM, Rf=0.68.

Example 9

The Synthesis of Intermediate I, (piq)$_2$ Ir(acac)

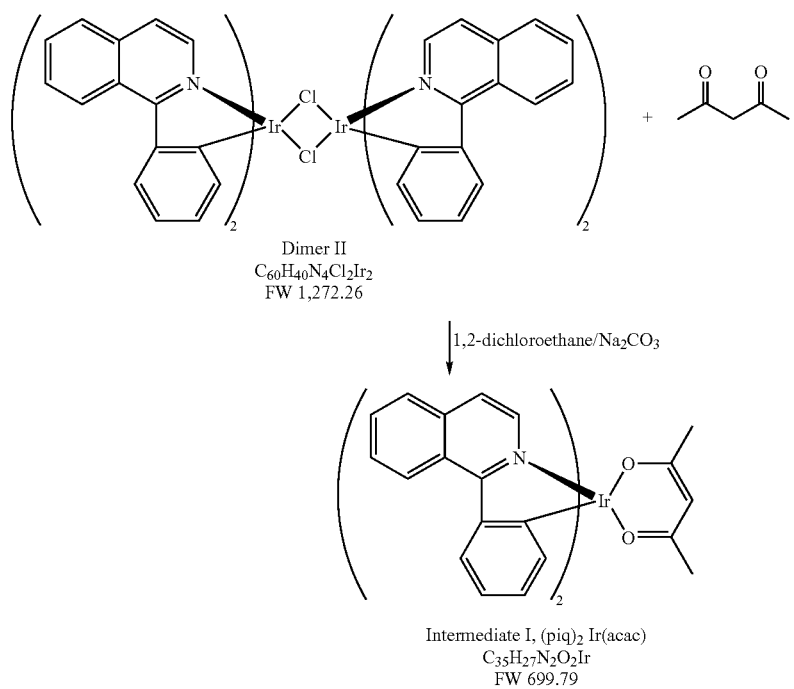

Synthetic scheme

Dimer II
$C_{60}H_{40}N_4Cl_2Ir_2$
FW 1,272.26

1,2-dichloroethane/Na$_2$CO$_3$

Intermediate I, (piq)$_2$ Ir(acac)
$C_{35}H_{27}N_2O_2Ir$
FW 699.79

Procedure:

A 500 mL 3-neck round-bottom flask was fluxed with nitrogen for 30 minutes, and 250 mL of 1,2-dichloroethane was poured in and the content was de-gassed with nitrogen bubbles for 30 minutes. After that, 12.72 g of Dimer II, (piq)$_2$Ir(μ-Cl)$_2$Ir(piq)$_2$ (10 mmol, 1.0 eq.), 2.50 g of 2,4-pentanedione (25 mmol., 2.5 eq.), and 5.30 g of sodium carbonate (50 mmol., 5.0 eq.) were added. The resulting red suspension was heated to reflux for 24 hours, and then allowed to cool down to room temperature.

The solvent was stripped off on a rotary evaporator and the red solid residue was added with methanol. The resultant red precipitates were filtered, washed with methanol, hexane and methanol, and dried under suction and in the air for the night. 9.89 g of a red solid was collected at the end, and it was purified by a silica gel column with DCM as an eluent. 8.49 g of a red crystalline solid (TLC DCM, Rf 0.72) was obtained with the yield of 60.7%.

Example 10

The Synthesis of Compound V (odz) Ir(piq)₂

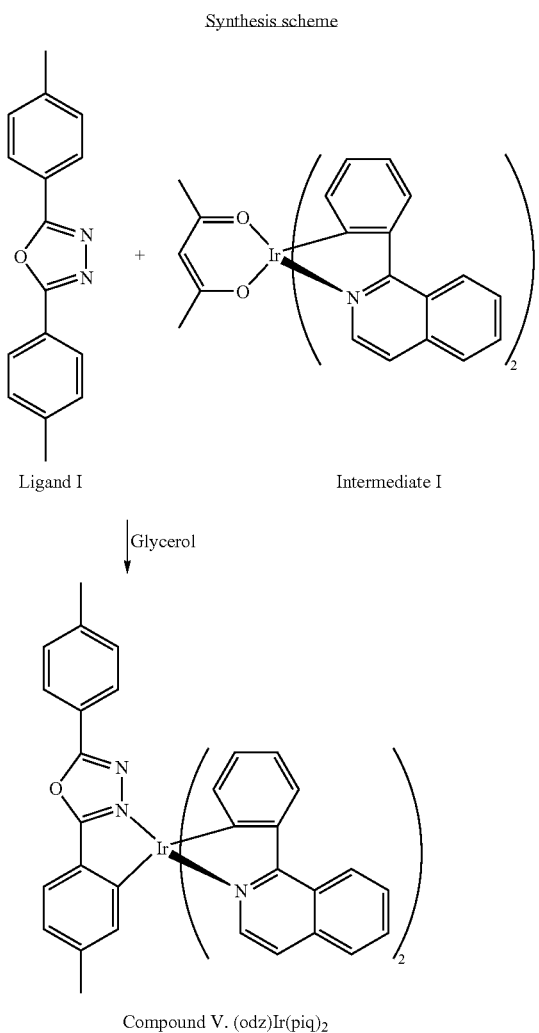

Compound V. (odz)Ir(piq)₂

Procedure:

A 100 mL one-neck flask was fluxed with nitrogen for 30 minutes. 20 mL of glycerol, (piq)₂Ir(acac) (Intermediate I, 0.70 g, 1 mmol.), 2,5-bis(p-tolyl)-1,3,4-oxadiazole (Ligand I, 0.50 g, 2 mmol.) were added and the resulting deep red solution was heated to reflux for 24 hours.

The solvent was then stripped off by a rotary evaporator, and the red solid residue was purified by a silica gel column with DCM as an eluent. 0.16 g of red powder was collected, which showed a saturated red color emission under UV-illumination.

Example 11

OLED Device Fabrication

Figure 5:
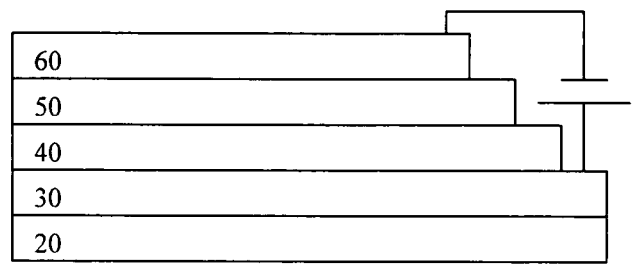
FIG. 5 shows a light emitting device (10) having compound I $(odz)_2Ir(acac)$ as the emitting material. In the device (10), (20) represents a glass substrate, the anode (30) is a layer of ITO, (40) represents a layer of PEDOT working as a hole transport materials, (50) is a layer of Compound I $((odz)_2Ir(acac))$ in polyfluorene working as the light emitting layer and the cathode (60) is formed by a layer of Ag/Mg.

An example for the fabrication of light emitting diodes is provided herein to demonstrate. the applications of the invented materials in opto-electronic devices. As depicted in FIG. 5, the OLED made by using compound I ((odz)₂Ir (acac)) according to this invention has a layered structure of ITO/PEDOT (40 nm)/polyfluorene:Compound I (80 nm)/ Mg—Ag (100 nm).

Device fabrication and testing experiments were carried out in a dry-box with a controlled N₂ atmosphere at room temperature. The fabrication procedure is given below. A 40-nm-thick layer of poly (enthylendioxythiophene):poly (styrene sulfonic acid) (PEDOT:PSS, Bayer Batron 4083) was spin-coated (at 2000 rpm) onto pre-cleaned ITO-glass substrates. Next, a polyfluorene solution in toluene containing compound I ((odz)₂Ir(acac)) (ratio of compound I:polyfluorene=1:20) was spin-coated at room temperature under ambient conditions to form a thin film of about 80 nm. The solvent was thoroughly removed by subsequently baking the samples on a hot plate. The Mg—Ag cathode (100 nm thick) was then deposited through a shadow mask at a chamber base pressure of less than $10^{-6}$ Torr.

Thickness of the layers was determined using a crystal thickness monitor. Current density (I) vs. voltage (V) measurements were obtained using a Keithley 236 source measurement unit. Electroluminescence (EL) spectra of the devices were recorded with a Photo Technology International PTI Fluorescence Master System.

Figure 6:
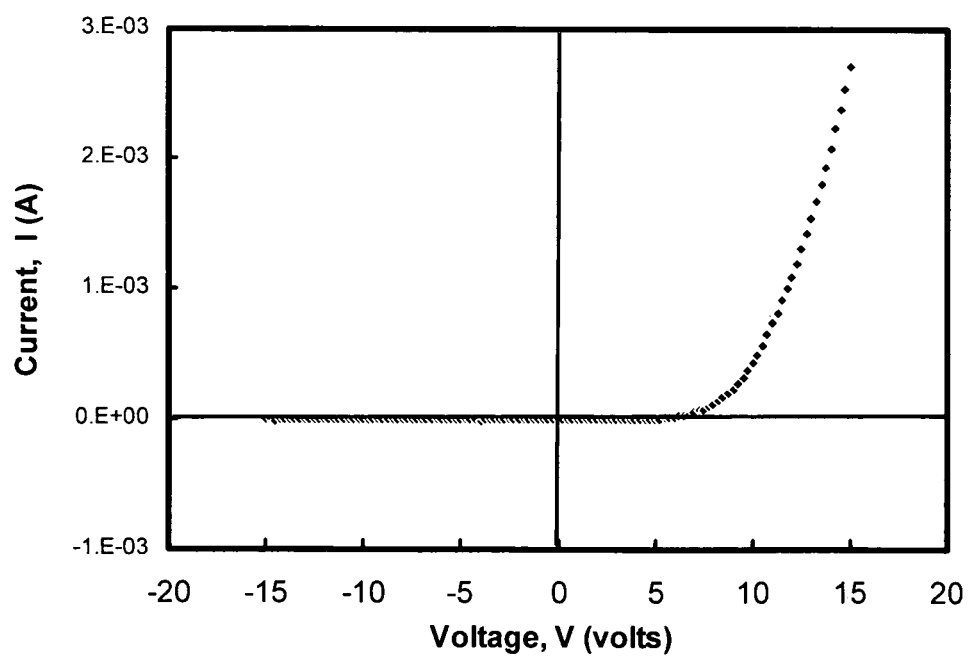
FIG. 6 shows the current-voltage characteristics of the device (10) shown in FIG. 5.
Figure 7:
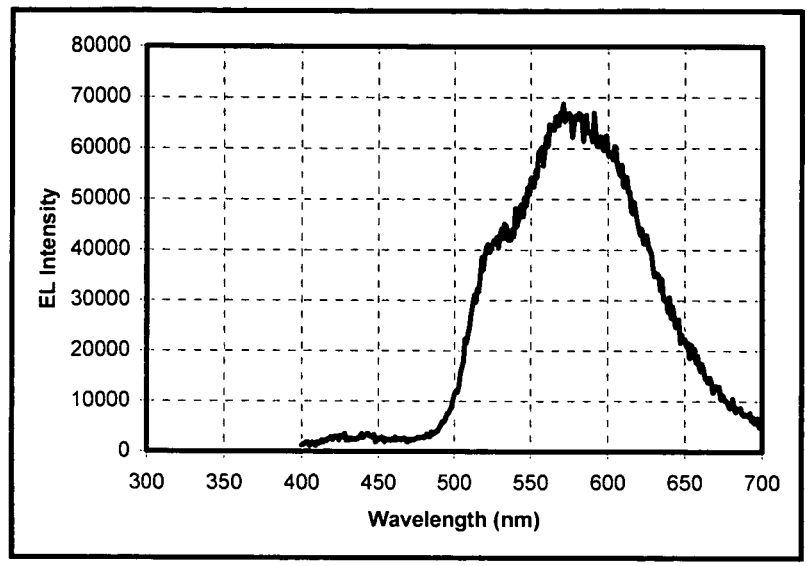
FIG. 7 shows the electroluminescent spectra for two OLED devices: (a) an OLED with a layer structure (10) given in FIG. 5 and with compound I in polyfluorene as the light emitting layer (50); (b) polyfluorene (without compound I) as the emitting layer (50). A clear shift in light wavelength is evident between the two devices.
Figure 7:
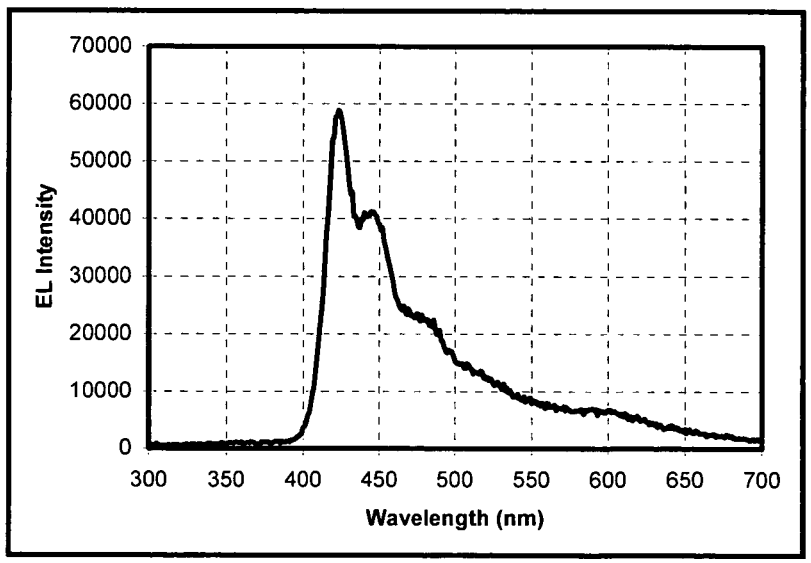

FIG. 6 presents the I-V characteristics of the device shown in FIG. 5. It demonstrates a typical diode behavior. FIG. 7 shows the electroluminescent spectra for two OLED devices: (a) an OLED with a layer structure (10) given in FIG. 5 and with compound I in polyfluorene as the light emitting layer (50); (b) polyfluorene (without compound I) as the emitting layer (50). A clear shift in light wavelength is evident between the two devices.

While the present invention is described with respect to particular examples and preferred embodiments, it is understood that the present invention is not limited to these examples and embodiments. The present invention as claimed therefore includes variations from the particular examples and preferred embodiments described herein, as will be apparent to those skilled in the art.

What is claimed is:

1. A metallic complex of the Formula I

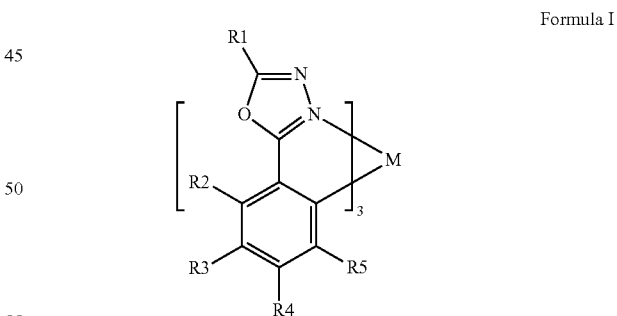

Formula I wherein M is a metal with an atomic weight of greater than 40; each of R1, R2, R3, R4, and R5 is, independently, H, alkyl, alkenyl, alkynyl, aryl, alkylaryl, CN, perfluoroalkyl, trifluorovinyl, $CO_2R$, $C(O)R$, $NR_2$, $NO_2$, OR, halo, heteroaryl, substituted aryl, substituted heteroaryl or a heterocyclic group, and additionally, or alternatively, any one or more of R2 and R3 or R3 and R4, or R4 and R5, together form, independently, a fused 5- to 6-member cyclic group, wherein said cyclic group is cycloalkyl, cycloheteroalkyl, aryl, or heteroaryl, and wherein the fused 5- to 6-member cyclic group may be optionally substituted with one or more of alkyl, alkenyl, alkynyl, alkylaryl, CN, perfluoroalkyl, trifluorovinyl, CO₂R, C(O)R, NR₂, NO₂, OR, halo; each R is independently H, alkyl, alkenyl, alkynyl, alkylaryl, and aryl.

2. A metallic complex of the Formula I as defined in claim 1, wherein R2, R3 and R5 are H.

3. A metallic complex of the Formula I as defined in claim 1, wherein R1 is aryl, or alkyl, or halo.

4. A metallic complex of the Formula I as defined in claim 1, wherein R2 and R4 are halo.

5. A metallic complex of the Formula I as defined in claim 1, wherein M is Ir.

6. A light emitting device which comprises an anode, a cathode and the metallic complex of the Formula I as defined in claim 1 between the anode and cathode.

7. A photovoltaic device which comprises the metallic complex of the Formula I as defined in claim 1 as an electron acceptor or light absorber.

8. A phosphorescence device for security and labeling which comprises the metallic complex of the Formula I as defined in claim 1.

9. A metallic complex of the Formula I

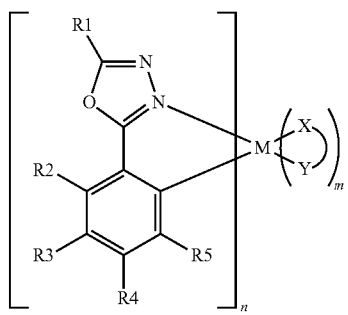

wherein M is a metal with an atomic weight of greater than 40;

each of R1, R2, R3, R4, and R5 is, independently, H, alkyl, alkenyl, alkynyl, aryl, alkylaryl, CN, perfluoroalkyl, trifluorovinyl, CO₂R, C(O)R, NR₂, NO₂, OR, halo, heteroaryl, substituted aryl, substituted heteroaryl or a heterocyclic group, and additionally, or alternatively, any one or more of R2 and R3 or R3 and R4, or R4 and R5, together form, independently, a fused 5- to 6-member cyclic group, wherein said cyclic group is cycloalkyl, cycloheteroalkyl, aryl, or heteroaryl, and wherein the fused 5- to 6-member cyclic group may be optionally substituted with one or more of alkyl, alkenyl, alkynyl, alkylaryl, CN, perfluoroalkyl, trifluorovinyl, CO₂R, C(O)R, NR₂, NO₂, OR, halo; each R is independently H, alkyl, alkenyl, alkynyl, alkylaryl, and aryl, X^Y represent a ligand, n is 1, 2 or 3 and m is 0, 1, or 2, wherein m+n is equal or greater than 3;

with the proviso that X^Y is not of the formula

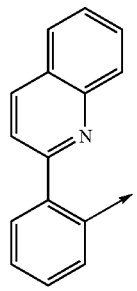

and derivatives thereof.

10. The metallic complex of claim 9, wherein X^Y is a ligand having an oxygen atom that is bonded to the metal atom M or of the formula

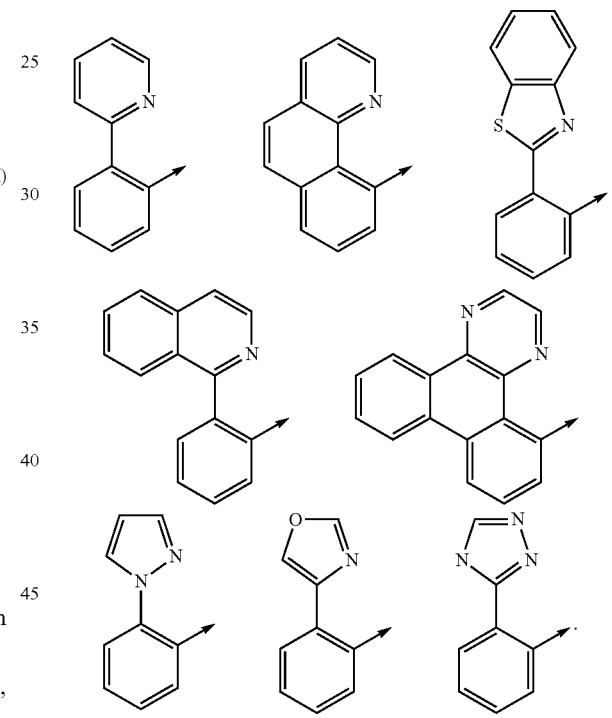

11. The metallic complex of claim 9, wherein X^Y is of the formula

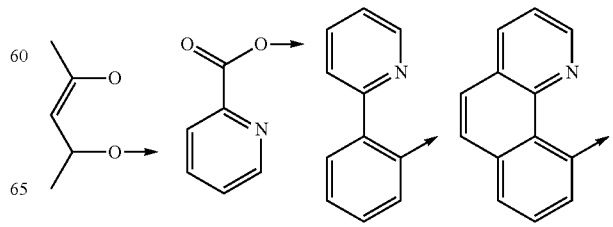

23
-continued

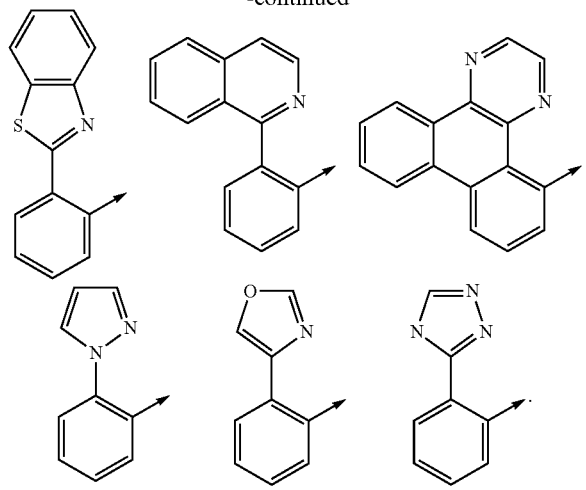

12. The metallic complex of the Formula I as defined in claim 11, wherein R2, R3 and R5 are H,
R1 is aryl, or alkyl, or halo,
R4 is halogen and
M is Ir.

13. The metallic complex of the Formula I as defined in claim 9, wherein R2, R3 and R5 are H and
R1 is aryl, or alkyl, or halo.

14. A metallic complex of the Formula I as defined in claim 9, wherein R2 and R4 are halogen.

15. A metallic complex of the Formula I as defined in claim 9, wherein M is Ir.

16. A light emitting device which comprises an anode, a cathode and the metallic complex of the Formula I as defined in claim 9 between the anode and cathode.

17. A photovoltaic device which comprises the metallic complex of the Formula I as defined in claim 9 as an electron acceptor or light absorber.

18. A phosphorescence device for security or labeling which comprises the metallic complex of the Formula I as defined in claim 9.

19. The metallic complex of claim 9, wherein X^Y is a ligand having an oxygen atom that is bonded to the metal atom M or a ligand having a carbon atom that is bonded to the metal atom M.

24

20. A metallic complex of the Formula I

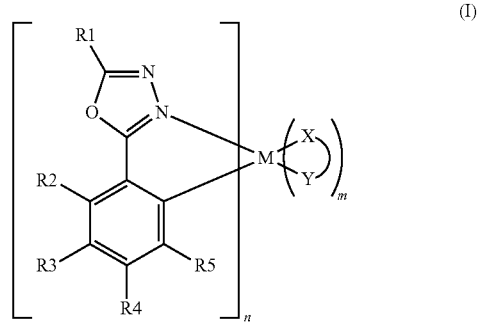

(I)

wherein M is a metal with an atomic weight of greater than 40;

each of R1, R2, R3, R4, and R5 is, independently, H, alkyl, alkenyl, alkynyl, aryl, alkylaryl, CN, perfluoroalkyl, trifluorovinyl, $CO_2R$, $C(O)R$, $NR_2$, $NO_2$, OR, halo, heteroaryl, substituted aryl, substituted heteroaryl or a heterocyclic group, and additionally, or alternatively, any one or more of R2 and R3 or R3 and R4, or R4 and R5, together form, independently, a fused 5- to 6-member cyclic group, wherein said cyclic group is cycloalkyl, cycloheteroalkyl, aryl, or heteroaryl, and wherein the fused 5- to 6-member cyclic group may be optionally substituted with one or more of alkyl, alkenyl, alkynyl, alkylaryl, CN, perfluoroalkyl, trifluorovinyl, $CO_2R$, $C(O)R$, $NR_2$, $NO_2$, OR, halo; each R is independently H, alkyl, alkenyl, alkynyl, alkylaryl, and aryl, X^Y represent a ligand selected from the group consisting of benzoquinoline, phenylbenzothiazolyl, naphthylbenzothiazolyl, thienylpyridine, benzothienylpyridine, phenyloxazoyl, diphenyloxazoyl, phenyl-isoquinoline, dibenzoquinoxaline, phenylpyrazolyl, phenyloxazole, phenyltriazole and derivatives thereof, n is 1, 2 or 3 and m is 0, 1, or 2, wherein m+n is equal or greater than 3.

21. The metallic complex of the Formula I as defined in claim 9, wherein X^Y represent a ligand selected from the group consisting of phenylpyridine, benzoquinoline, phenylbenzothiazolyl, naphthylbenzothiazolyl, thienylpyridine, benzothienylpyridine, phenyloxazoyl, diphenyloxazoyl, phenyl-isoquinoline, dibenzoquinoxaline, phenylpyrazolyl, phenyloxazole, and phenyltriazole.

* * * * *